United States Patent [19]

Hetrick

[11] Patent Number: 5,000,050

[45] Date of Patent: Mar. 19, 1991

[54] MASS-FLOW SENSOR USING AERODYNAMIC DAMPING

[75] Inventor: Robert E. Hetrick, Dearborn Heights, Mich.

[73] Assignee: Ford Motor Company, Dearborn, Mich.

[21] Appl. No.: 492,015

[22] Filed: Mar. 12, 1990

[51] Int. Cl.$^5$ .............................................. G01N 3/00
[52] U.S. Cl. .................................. 73/861.18; 73/704; 73/702; 73/32 A
[58] Field of Search ............. 73/861.18, 861.37, 32 A, 73/32 X, 704, 703, 701, 702

[56] References Cited

U.S. PATENT DOCUMENTS

| | | | |
|---|---|---|---|
| 4,024,759 | 5/1977 | Klinger et al. | 73/861.18 |
| 4,488,439 | 12/1984 | Gast et al. | 73/861.18 |
| 4,739,664 | 4/1988 | Hetrick | 73/704 |

Primary Examiner—Joseph A. Orsino
Assistant Examiner—Franklin V. Nguyen
Attorney, Agent, or Firm—Peter Abolins; Clifford L. Sadler

[57] ABSTRACT

A fluid mass flow sensor uses the effect of aerodynamic drag on a vibrating object. The drag damps the resonance oscillations of the vibrator in an amount proportional to the mass flow. An electronic feedback circuit associated with the mass flow sensor has the effect of allowing for fast response time despite the use of a high Q vibrator and allows for electronic calibration of the device.

12 Claims, 2 Drawing Sheets

MASS-FLOW SENSOR USING AERODYNAMIC DAMPING

BACKGROUND OF THE INVENTION

1. Field of the Invention

This invention relates to electrical circuit means for measuring the mass flow of an incident fluid using a resonantly vibrating object.

2. Prior Art

A key aspect of maintaining the correct ratio of air to fuel at the intake of fuel-injected internal combustion engines is measuring the mass flow (kg/sec.) of incoming air. From this, the amount of incoming oxygen can be inferred so that the correct amount of fuel can be injected. In one method, the well known hot-wire anemometer, utilizing the phenomenon of forced convection has seen considerable development. An alternate measurement technique, U.S. Pat. No. 4,024,759 issued to Klinger et al, teaches how the aerodynamic drag force, resulting from the incident flow of a gas on a resonantly vibrating object can be used to measure the mass flow of the incident gas. This method, which is extendable to fluids in general and may be classified in the category of drag as opposed to thermal anemometry, has several advantages over using the hot-wire anemometer both with regard to function and economy of manufacture. For example, the drag anemometer could be used to measure the mass flow of combustible-gas mixtures for which application of a hot-wire device might be unsafe.

With the vibrating object (e.g. in the form of a flat blade) in the flow, mass flow is determined by the amount by which the drag force damps the vibration. To measure mass flow, an actuator will be required to excite vibrations as well as a sensor to measure the amplitude of the vibration. Since the peak amplitude of a resonance vibration is inversely proportional to the damping, measurement of that amplitude will provide a measure of the mass flow. The mechanical vibrators may have a sharp resonance in the frequency domain. Said differently, they may be high-Q devices. If one measures peak amplitude to determine mass flow, the response time, T, for a step change in mass flow to change the amplitude is proportional to Q. Thus a high-Q device (which as discussed below offers desirable benefits) is realized at the expense of response time. To overcome this difficulty, a negative feedback control circuit is used to maintain ac vibrational amplitude constant despite damping. The control voltage used to accomplish this increases with flow-induced damping and measures mass flow. Because the vibrational amplitude does not change, response time is improved. U.S. Pat. No. 4,024,759 teaches such a circuit but employs complex digital circuitry.

U.S. Pat. No. 4,488,439 issued to Gast et al teaches improved analog circuitry, but employs band-pass filters which establish the desired response time of the device. Applicant's invention teaches an improved circuitry which simply maintains constant vibrational amplitude without band pass filters and thus realizes short response times.

In addition to flow-induced damping, all vibrators have inherent damping in zero flow due to frictional effects. Such effects would include viscous losses, for example, in epoxy layers or piezoelectric elements used to actuate or sense the vibrations. It is desirable for these inherent frictional effects to be low (resulting in a high Q vibrator) since they occur simultaneously with the flow-induced damping and reduce sensitivity to that damping component especially at low flows. The patent to Gast et al teaches circuitry to effectively eliminate the inherent damping by electronically subtracting a signal proportional to the inherent damping from that voltage which measures total damping. The method employed involves the use of an additional electrical oscillator as well as band-pass filters which will increase time response. It would be desirable to accomplish this function with a simpler (no additional oscillator is required) and faster (no band-pass filter is required) supplement to the feedback circuit. It would also be desirable to allow for a calibration of the response of the device to overcome component and manufacturing variations. These are some of the problems this invention overcomes.

Further, due to component and manufacturing variations, the exact resonant frequency of the mechanical vibrator may vary somewhat with each device. Circuits of the prior art allow one to maintain oscillation at the resonant frequency despite this variability. However, the resonant frequency of the device may change during use. For example, dust or ice may accumulate on the vibrating element thereby changing its effective mass and resonant frequency. Although existing circuitry would track this change (to the extent allowed by band-pass filters) such in-use change is undesirable. The reason is that the amplitude of peak vibration (which is held constant) is inversely proportional to the product of the total damping coefficient (C) and the angular resonance frequency ($\omega_o$). After an initial calibration corresponding to a particular initial $\omega_o$, any further change in $W_o$ during use cannot be distinguished from a change in damping resulting from flow. Thus, it is desirable to keep $\omega_o$ constant after an initial calibration. It would be desirable to allow the resonance frequency to be "pulled" and hence maintained at a constant value during operation thereby preserving a fixed calibration. Within the frequency "pulling" circuit is a voltage indicating the extent of the frequency modification. This information may be useful in some applications. If it is not, a simplification is possible in which the velocity of the blade is held constant rather than the amplitude. In this method the mass flow can be measured independently of small changes in the resonant frequency which may occur due to manufacturing variations or in process use. This is another problem this invention overcomes.

SUMMARY OF THE INVENTION

This invention is a circuit means that enables the operation of a mechanically vibrating device appropriately placed in a moving fluid, for determining the mass flow (kg/sec.) of that fluid. The vibrator is usually in the form of a thin flat plate which has one attached electromechanical means for exciting a resonant vibration of the plate and a second electromechanical means attached to the plate for sensing the amplitude (or velocity or acceleration) of the induced vibration. Preferentially, the plate should be positioned transversely so that flow is incident normally upon the large area of the plate. As an example, the vibrator could take the form of a small, thin cantilever blade. The fundamental resonance of the blade could be actuated by a ceramic piezoelectric bimorph to which the fixed end is attached while the amplitude is sensed by a thin polymeric piezoelectric element also attached near the fixed end of the blade.

The circuit means of the invention has an ac output which drives the actuator of the resonance vibration and an ac input from the sensor of the vibrational amplitude. The analog circuitry includes three components to perform differing functions. A first component produces an ac voltage of proper frequency and amplitude to drive the vibrating device at its resonance frequency and at constant amplitude despite the fact that the resonance frequency may be changing somewhat during operation and the damping may vary with flow conditions. The reason for doing this is twofold. First, the damping (and accordingly the mass flow information) affects the vibrational amplitude at resonance most sensitively. Thus, it is advantageous to operate at this frequency. Second, it proves to be advantageous to work with a high Q (from 100-500) mechanical oscillator for sensitivity to mass flow. However, changes in the amplitude of a high Q oscillator are only accomplished with a time constant that increases with the Q. To prevent this time constant from becoming unacceptably long for the application, one can use a feedback control circuit to maintain this amplitude at a constant value despite variable damping. In this way the time constant can be significantly reduced despite the high Q while a voltage within the control circuit serves to measure the damping and the mass flow.

A second component of the circuit serves to adjust the sensitivity of the device to flow thereby allowing different devices to be calibrated to produce identical sensitivities. This is accomplished by adjusting the phase of the signal from the amplitude sensor to have exactly the phase of the velocity of the vibrating device. At resonance, this signal is then in phase with the drive voltage. This signal is amplified, and using an adder circuit, is applied to the actuator simultaneously with the output of the first component of the circuit. By adjusting the relative contributions of the two components, the control circuitry of the first component will necessarily execute proportionally greater (if more second component is added) or lesser (if less second component is added) variation to maintain a constant vibrational amplitude during flow. It can be shown that this has the same effect as if the second component were not present but the Q of the device had been raised or lowered. The higher Q corresponds to the case where there is greater variability in the first circuit component.

The third component of the circuit allows for the resonance frequency of the oscillator to be "pulled" or varied during operation. Although the first component will keep the oscillator vibrating at resonance even if that frequency varies, it may prove desirable to keep the resonance frequency unchanged after an initial calibration. Thus, for such mechanical oscillators, the amplitude of vibration is inversely proportional to the resonance frequency as well as a damping coefficient. Accordingly, if that frequency changes, for example, due to the accumulation of dirt on the vibrator, the resulting change in amplitude cannot be distinguished from that due to damping. Thus, it is desirable to keep the resonance frequency fixed. This is accomplished by adjusting the phase of the signal from the amplitude sensor to have exactly the phase of vibrator acceleration, comparing this electrically with a reference signal specifying the desired signal and applying the amplified output of the actuator drive through a third input of the same adder circuit by which the first and second components are simultaneously applied. The effect of this addition is either to increase the mass (lower the resonance frequency) or the spring constant (increase the resonance frequency) by an amount proportional to the amplitude of the third component.

If it is not desired to know the change in the resonance frequency which would have been produced without the frequency "pulling" (information contained in the third circuit component), a simplification arises. The device is modified so that the velocity rather than the amplitude of the blade is held constant. Concurrently, the third component of the circuit is eliminated. With this modification, the circuit produces an output proportional to mass flow but independent of changes in resonant frequency which may arise from the accumulation of condensates on the blade.

DETAILED DESCRIPTION OF THE INVENTION

Figure 1:
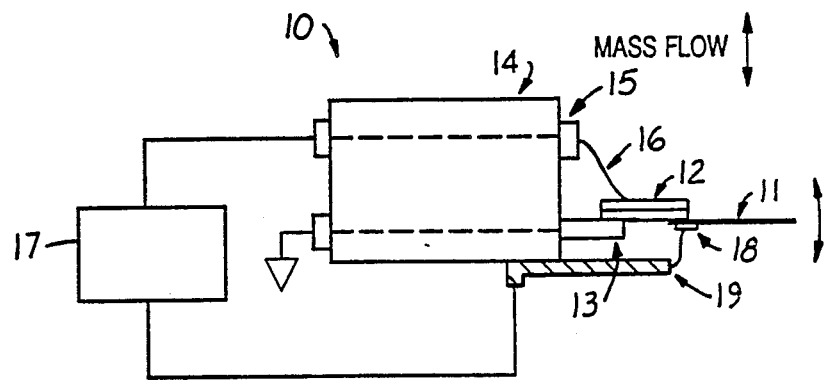
FIG. 1 shows a side view of a vibrating cantilever structure with attached circuitry which can be used to detect mass flow, with mass flow incident to the top or bottom of the blade.

Most vibrating objects, at least in a frequency region near a resonance frequency ($f_o$), can be approximated as a simple harmonic oscillator (SHO). Thus a long, thin, cantilever blade, whose vibrational motion is described by the "beam equation" rather than the SHO differential equation, can nonetheless be closely approximated as a SHO near a resonance using an effective mass (M), spring constant (k) and damping coefficient (C) which are different for each resonant mode. As an example, near the fundamental resonance of such a cantilever, the motion is approximated by the SHO equation $$M\ddot{X} + C\dot{X} + kX = F_P \quad (1)$$

where X is the transverse displacement of the tip of the blade and $F_P$ is the sinusoidal driving force. The well known solution of this equation is described by such parameters as a maximum amplitude X(max) and maximum velocity $\dot{X}$(max) are given by $$X(\max) = F_p/C\,\omega_o \quad (2)$$
$$\dot{X}(\max) = F_p/C$$
where
$$\omega_o = 2\pi f_o = (k/M)^{\frac{1}{2}} \quad (2')$$

and a Q (quality factor) given by $$Q = \omega_o M/C. \quad (3)$$

and a time constant ($\tau$) for the amplitude to respond to a step change in the amplitude of $F_P$ given by $$\tau = Q/\omega_o. \tag{4}$$

In the presence of a fluid flow transverse to the large area of the blade, a stationary cantilever blade (to continue with this particular example) is subject to an additional aerodynamic force (drag force) $F_d$ given by $$F_D = \tfrac{1}{2}\rho C_D V^2 A \tag{5}$$

where $\rho$ is the density of the fluid, A is an effective cross-sectional area of the blade, V is the fluid velocity relative to the blade and $C_D$ is the drag coefficient which is a function of the Reynold's number (R) describing the flow past the blade. Note that this description assumes that the incident flow is substantially non-turbulent. For a "bluff body" like the blade, experiment shows $C_D \sim 1/V^n$ where $0 \leq n \leq 1$ when $R \leq 1200$. For R greater than this value $C_D$ is independent of V, and $F_D$ is proportional to $V^2$. When the blade is vibrating, it is the relative velocity which determines $F_D$ so that $$F_D = \tfrac{1}{2}\rho C_D A (V-\dot{X})^2 \approx \tfrac{1}{2}\rho C_D A V^2 - \rho C_D A V \dot{X} +. \tag{6}$$

where the last term in the expansion has been dropped because we anticipate an application where V (on the order of 1-100 m/sec) is much larger than the maximum blade velocity $\dot{X}$(max) ($=\omega_o$ X(max), typically $<1$ mm/sec). Assume that the time variations in V are relatively slow compared to the vibrational frequency of the blade (1-5 kHz). Then the first term of (6) represents a "constant" force which will produce a bending of the blade to a new steady-state position about which the vibrational motion occurs. For important applications this term proves not to be large enough to affect the operation of the vibrator (e.g. it does not break the blade, does not change the resonance frequency or affect the vibrational amplitude) and can be neglected when analyzing vibrational motion. This would not be true if the incident flow is so rapidly varying that it contains frequency components at the resonant frequency of the blade as might happen if the flow were turbulent. The second term is proportional to $\dot{X}$ and thus corresponds to a damping of the blade proportional to $\rho V$. When the latter term is multiplied by the cross-sectional area of the tube through which the fluid flows, one computes the mass flow of the fluid in (kg/sec). Thus this aerodynamic damping term serves to measure the mass flow. Neglecting the first term one finds $$M\ddot{x} + (C + \rho V C_D A)\dot{x} + kx = F_p, \tag{7}$$

so that $$X(\max) = \frac{F_p}{(C + \rho V C_D A)\omega_o}. \tag{8}$$

and the two damping terms add to determine the maximum vibrational amplitude. Thus measuring this amplitude, and its variation with flow, forms the basis of a vibrational mass-flow sensor.

Equations (8) and (4) can be used to explain why all of the features of the electrical circuit to be described below are desirable. First, one wants to vibrate on resonance so that a simple relation like equation (8) holds. Second, it is desirable that $C < \rho V C_D A$ so that one is more sensitive to $\rho V$ variations. Low C results in a high Q device which by equation (4) implies a long time constant. Should this time constant be unacceptably long for the application, it is desirable to work in a mode where X(max) is electrically held fixed while $F_P$ is varied to achieve this condition. In this circumstance $F_P(V) \sim (C + \rho V C_D A) \omega_o$ and one can obtain $\rho V$ from a measurement of $F_P(V)$. Since the amplitude does not change, the response time is not determined by Q but rather by components in the feedback circuit required to keep X(max) a constant. Significant reductions in response times can be achieved by this method. Third, manufacturing variations in C are to be expected, and this will change the calibration by which $F_p(V)$ determines mass flow. Thus it is desirable to have a method of electrically simulating a change in C so that all devices can be brought to the same C value and calibration. This can be done with feedback circuitry. Fourth, it is also clear that $F_p(V)$ varies linearly with $\omega_o$ so that if $\omega_o$ changes after an initial calibration, that calibration is lost. Thus, it is desirable to have the ability to keep $\omega_o$ constant. This can be accomplished simultaneously with the frequency "pulling" circuitry described below. Should it prove unnecessary to know the amount by which the resonant frequency has changed during operation, a simplification arises. The device is modified so that the maximum velocity of the blade can be held constant instead of the maximum amplitude. In this case one can show that $F_p(V)$ is independent of resonance frequency allowing the latter to vary due to in process or manufacturing variations.

Although it is possible to discuss the circuitry in the context of a generalized vibrating structure, we will be specific and choose the vibrating cantilever structure described above. FIG. 1 schematically shows a piezoelectrically driven, vibrating cantilever device 10, as described in U.S. Pat. No. 4,739,664 issued to Hetrick. It includes cantilever blade 11 which is attached to the end of a ceramic piezoelectric bimorph 12 which in turn is attached in a cantilevered manner to an extension 13 of a support structure 14. Structure 14 contains three electrical feedthroughs. Two of these are used for applying an alternating emf to opposite faces of bimorph 12 for the purpose of driving blade 11 at its fundamental resonance frequency. One feedthrough 15 is shown with a lead wire 16 extending to the upper surface of bimorph 12. For convenience, extension 13 to which one face of bimorph 12 is attached can be an electrical conductor that serves as the other feedthrough. A source of oscillating EMF from feedback circuitry 17 attached to these feedthroughs is tuned, as described below, to the fundamental resonance frequency (or the frequency of an overtone mode) of the cantilever structure. That mode is one in which the free end of cantilever blade 11 has a maximum vibrational amplitude while the only node is at the point of support on bimorph 12. As an example the blade can be made of 50 $\mu$m thick steel with a length of 0.5 cm and a width of 0.15 cm. The bimorph of comparable dimensions can be a laminated structure with an active piezoelectric component made from lead zirconate titanate.

As an input to the feedback circuit, one needs a signal proportional to the amplitude of vibration of the blade (or at least a signal which is phase shifted from that of the amplitude by a constant amount. To implement this, a small piece of polymeric piezoelectric film 18 (such as is available from Pennwalt Corp.) is attached (using, e.g., Ag paste) near the fixed end of the blade on cantilever 11 shown in FIG. 1. A wire 19 attached to the support structure 14 makes contact to the upper surface of polymeric piezoelectric film 18 while contact to the lower surface is assumed to be made through the blade to the conducting feedthrough 13. Such feedback output from polymeric piezoelectric film 18 is applied to a feedback electronics package 17 which is discussed below. This arrangement does not greatly impede the vibration of the blade. When the blade vibrates, the stretching and contraction of polymeric piezoelectric film 18 produces an oscillatory electrical output that is proportional to the amplitude of vibration.

Figure 2:
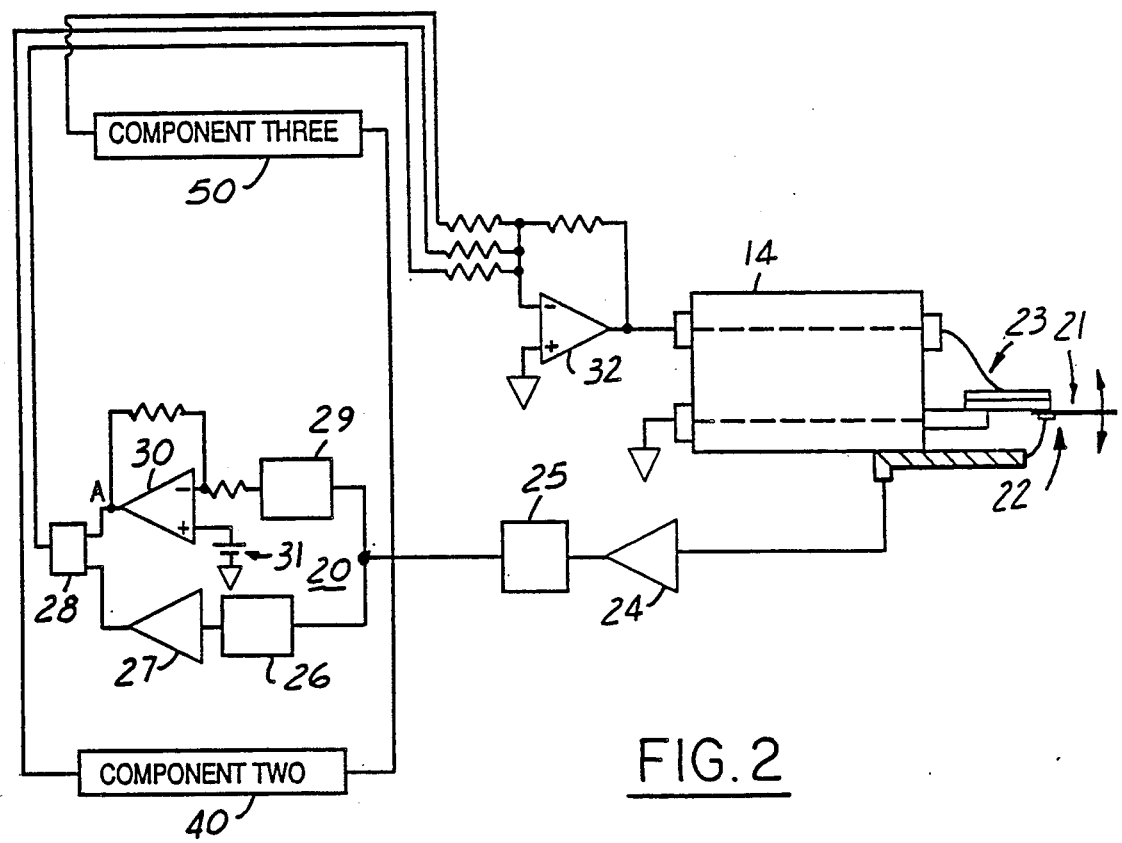
FIG. 2 shows a schematic diagram of the vibrating cantilever structure with an expanded view of some of the feedback circuit including component one for maintaining the vibrator on resonance with a constant vibrational amplitude.

FIG. 2 shows in detail a first component 20 of the feedback circuitry which is used to maintain vibrator 21 on resonance at a constant amplitude of vibration. Before processing by either of the three principal components of the feedback circuitry, the signal from the polymeric piezoelectric element 22, or equivalent amplitude sensor, is first detected and amplified by preamplifier 24. The output of 24 is then passed through a phase-shift circuit 25 so that the phase of the signal can be adjusted to correspond to the phase of the amplitude of vibration. This adjusts the signal for any phase shifts which may have occurred in the preamplifier stage. This is done by connecting an external oscillator to the ceramic bimorph 23, or equivalent vibration actuator, adjusting the frequency of the oscillator to that corresponding to the vibrator resonance, and adjusting the phase of the amplitude signal (using phase-shift circuit 25) until it lags the phase of the actuator signal by 90°. A property of a SHO is that the phase of the vibrator amplitude lags the phase of the actuator by 90° at resonance.

The output of phase-shift circuit 25 is then applied to two branches of first component 20. One branch consists of a phase-locked loop circuit 26. This device compares the incoming signal with the oscillatory output of a local oscillator 26 and adjusts (through internal feedback) the frequency and phase of the local oscillator so that it is always 90° in advance of the phase of the incoming signal. With the specified input however, this is just the condition which characterizes the actuator drive signal at the resonance of a SHO. The output of local oscillator 26 will be used to actuate the vibrator and thus maintain that vibrator on resonance even though that resonance may vary due to manufacturing variations or due to changes in the vibrator (such as dirt deposits) during operation. The output of oscillator 26 is then amplified by amplifier 27 as desired. The output of amplifier 27 then forms one input of multiplier 28.

To maintain the vibrational amplitude constant, despite varying damping due to flow, the output of phase-shift circuit 25 is also fed to the second branch of the feedback circuit whose first component is a demodulator 29 containing a full wave rectifier and low pass filter. The low pass filter determines the response time of this component of the feedback circuit. The dc output of demodulator 29 (whose magnitude is linearly proportional to the ac amplitude of the vibrator amplitude signal) is fed to one input of a negative feedback amplifier 30 whose other input is a reference dc voltage 31 which can be chosen arbitrarily and serves to set the desired vibration amplitude of vibrator 21. The output of feedback amplifier 30 is applied to the second input of multiplier 28. The output of multiplier 28 is then applied to one of three inputs of a summing amplifier 32 whose output is used to drive the ceramic bimorph. If the vibrational amplitude of vibrator 21 should increase (decrease) as a result of a change in damping during flow, the output of feedback amplifier 30 will decrease (increase) and through the action of multiplier 28 will vary the amplitude of the ac drive voltage by just that amount which will bring the amplitude back to a value determined by the setting of reference dc voltage 31. In this way, first component 20 keeps vibrator 21 on resonance at a constant amplitude.

The signal which is proportional to mass flow is the dc voltage appearing at point A. This can be shown by a simple model. Assume in equation (7) that $F_p$, a sinusoidal driving force at $f_o$, is proportional to the ac voltage applied to the bimorph. Let this voltage consist of an ac component $\sin \omega_o t$ of unit amplitude (set by amplifier 27) at the resonant frequency (determined by oscillator 26) and multiplied by an amplitude $V_A$, corresponding to the voltage at point A, by multiplier 28. Thus $F_p \sim V_A \sin \omega_o t$. The action of component one (20) is to keep X(max) at a constant value. Using equation (8) one finds $$V_A \sim \omega_o (C + \rho V C_D A). \tag{8'}$$

Thus the voltage at point A serves to linearly sense the mass flow $\rho V$. This occurs with a rapid response time despite the use of a high Q oscillator since the amplitude does not vary. A component two (40) of the feedback circuit will show how to simulate the electrical variation of C, the constant offset in equation (8'), and a component three (50) will show how to electrically vary the proportionality constant so that each device can be calibrated. The outputs of these additional components 40 and 50 are applied to the other inputs of adder circuit 32.

Figure 3:
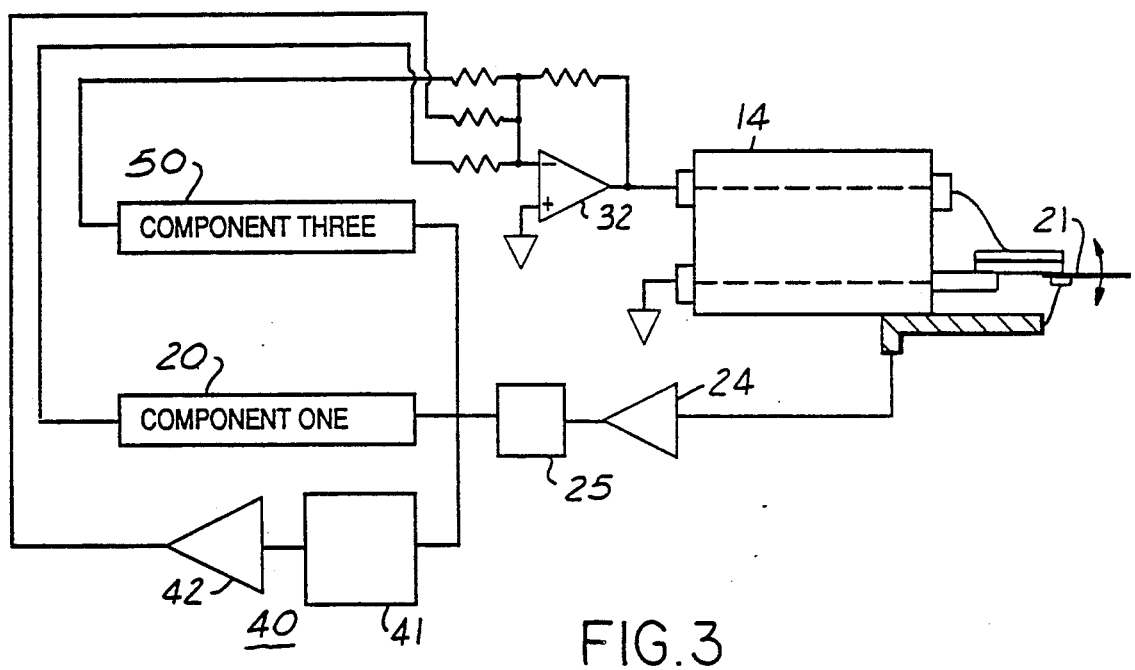
FIG. 3 shows a schematic diagram of component two of the feedback circuit whose action is to electronically modify the Q of the vibrator for calibration purposes.

To electrically calibrate the device (effectively adjusting the inherent Q of the vibrator) second component 40 of the feedback circuitry shown in FIG. 3 is used. The output of phase shifter 25 is passed through another phase shift circuit 41 so that the signal leads (+) or lags (−) the amplitude signal by ±90° and is thus proportional to the velocity of the blade (the velocity of a SHO leads the amplitude by 90° at all frequencies). The + (−) sign is chosen if one needs to increase (decrease) the Q. This signal is then amplified by a desired amount (amplifier 42) and applied to a second input of the adder circuit 32. At resonance, this added component is either in, or 180° out of, phase with the drive signal originating from the first component of the feedback circuit, since as mentioned before, the driving signal of a SHO advances in phase by 90° relative to the amplitude at resonance.

This added driving term can be moldeled by adding another driving term $F_v = C'' X$ to the right hand side of equation (7) so that one has $$M\ddot{X} + (C + \rho V C_D A)\dot{X} + kX = F_P + C'' \dot{X} \tag{9}$$

or $$M\ddot{X} + (C - C'' + \rho V C_D A)\dot{X} + kX = F_P \tag{10}$$

where $C''$ is determined both in sign and magnitude by the sign and amount of amplification provided in component two of the feedback circuit. From equation (10) it can be seen that by adjusting $C''$ electrically, one could adjust the sum $C - C''$ to some constant value thereby allowing for some manufacturing variability in $C_v$ while retaining the ability to calibrate the device. If one solves equation (10) for $F_P$ at resonance in terms of X(max) which is held constant by component one, one finds $$F_P(V) = (C - C'' + \rho V C_D A)\omega_o X(\text{max}). \tag{11}$$

Consider the case where one wants a high Q device for high sensitivity to at low V. One adjusts C" so that the C−C" sum is small but positive. At zero flow, $F_P$, the actuator drive provided by component one, will be small as if one were driving a high Q vibrator. As V increases, $F_P$ (V) will increase by an amount proportional to $\rho V$.

Figure 4:
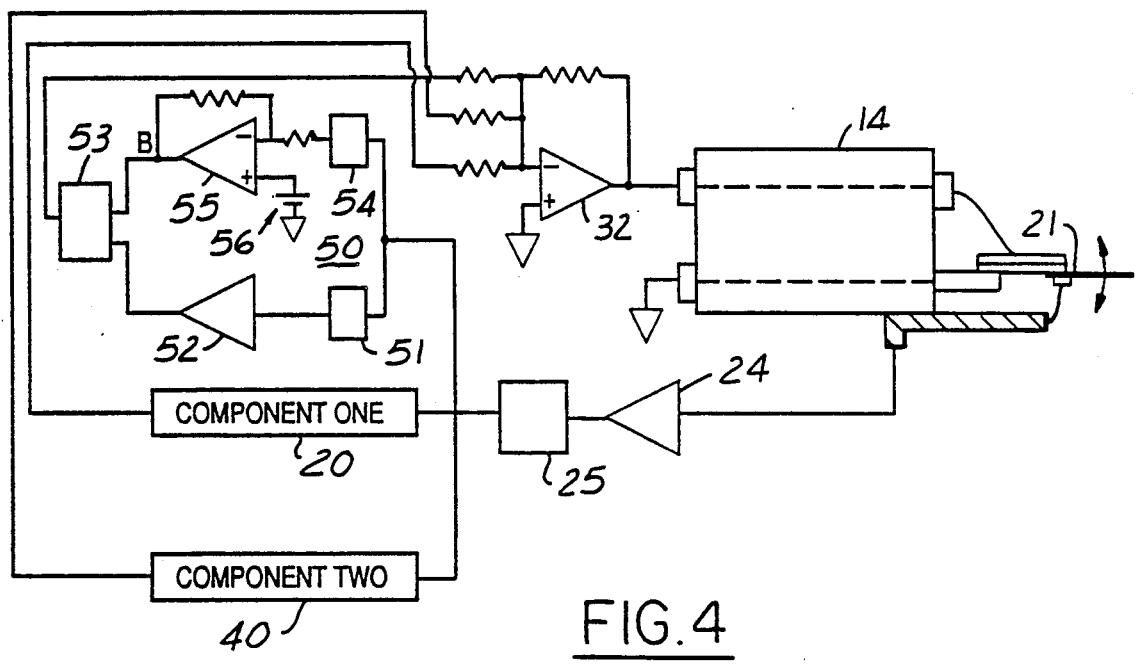
FIG. 4 shows a schematic diagram of component three of the feedback circuit whose action is to electronically maintain the vibrator at a constant resonant frequency.

Third component 50, of the feedback circuit which allows one to maintain a constant $\omega_o$ despite small changes in the effective mass (for example, due to the deposit of dirt on the blade) or spring constant of the blade during operation is shown in FIG. 4. The signal from phase shifter 25 is split into two components. The first is passed through a phase shifter 51 which adjusts the signal so that it is in phase with the acceleration (X) of blade 21. This amounts to a 180° phase lead or lag from the amplitude signal. This signal is then amplified (amplifier 52) as desired and the resultant signal forms one input of multiplier 53. The second component is demodulated by passing it through a frequency to voltage converter 54. This voltage is then compared with a reference voltage 56 (which determines the desired resonance frequency in the negative feedback amplifier 55) and the amplified dc output applied to the other input of the multiplier 53. The output of the multiplier is then added to the actuator drive signal through the third input of the adder circuit 32. If the resonance frequency should exceed or fall below the desired value, the output 55 will adopt increasing −or+voltages with which to multiply the ac signal (~X) at the other multiplier input. When this signal is applied to the actuator, it will serve to "pull" the resonance frequency back to the value determined by 56.

This effect can be modeled by adding another driving term $F_a = C''' X$ to the right hand side of (7) so that one has $$M\ddot{X} + C\dot{X} + kX = F_P + C''' X \tag{12}$$

or $$(M - C''')\ddot{X} + C\dot{X} + kX = F_P \tag{13}$$

where C''' is determined both in sign and magnitude by the sign and amount of amplification provided by component three of the feedback circuit. For the present purpose a single damping coefficient C includes all of the damping terms (including that contributed by component two of the feedback circuit). From equation (13) it can be seen that by adjusting C''' electrically, one can adjust the sum (M−C''') to some constant desirable value. Equation (2') for the resonance frequency is now modified to $$\omega_o = (k/(M - C'''))^{\frac{1}{2}} \tag{14}$$

showing that one now has some electrical control over $\omega_o$. Component three of the feedback circuit is designed to keep $\omega_o$ a constant through adjustments in C''' despite the fact that k or M may change slightly during use of the device.

To summarize the operation of the entire feedback circuit, a simple analysis similar to the one leading to equation (8') yields $$V_A = b(C - C'' + \rho V C_D A)(k/(M - C'''))^{\frac{1}{2}}. \tag{14}$$

Here b is a proportionality constant. The sensor output $V_A$ is linearly proportional to the mass flow $\rho V$, with an offset C−C" which is electrically adjustable for calibration and a multiplicative term which affords a further adjustment of the proportionality constant.

In the above method, third component 50 of the feedback circuit "pulls" the resonant frequency back to its original "calibrated" value should it vary during operation. A voltage at point B (see FIG. 4) is available for monitoring the amount of feedback voltage required to do this. This voltage, in turn, measures the amount by which the resonant frequency would have changed if it were not electrically "pulled" and may, in itself, be a useful indicator of flow conditions. For example, there may be a condensate appearing on vibrator 21 which reduces the resonant frequency. A knowledge of the appearance or disappearance of this condensate could be useful. Should this information not be necessary, a simplification is possible in which third component 50 of the feedback circuit is not used. This occurs if one maintains the maximum velocity rather than the maximum amplitude of the blade constant during operation.

Referring to equation (2), one sees that the maximum value of the blade velocity is not inversely proportional to the resonant angular frequency. Thus, if this velocity is held constant (rather than the amplitude), one finds that the voltage at point A of first component 20 of the feedback circuit is given by $$V_A \sim (C + \rho V C_D A)$$

as in equation (8') without the resonance frequency as a coefficient. This method has the advantage that small changes in resonant frequency during operation will not affect the calibration of the device for mass flow measurements.

This method can be implemented simply. First, component three (50) of the feedback circuit is eliminated. Second, the device must be modified so that the transducer which senses the motion of the vibrating cantilever or other vibrating element is in fact sensitive to the instantaneous velocity rather than the instantaneous displacement of that element. Thus, the polymeric piezoelectric material mentioned above produces an AC response in phase with the displacement of the element. A transducer mechanism based on electromagnetic induction would be appropriate for generating an AC response in phase with the velocity of the blade. For example, after a thin insulating film layer is placed on one side of the blade (to prevent shorting to the blade), this might be accomplished by photolithographically depositing a planar multiturn coil along the length of the insulated side of the blade. In the presence of an external magnet (e.g., a small piece of a rare-earth magnet) an emf is induced in the coil which is in phase or 180° out of phase with the instantaneous velocity of the blade depending on the polarity of the magnet. The magnet would be adjusted for proper phasing. This signal is then sent to the first branch of component one of the feedback circuit and its amplitude is held constant by the action of the feedback circuit. Physically, if the resonant frequency of the blade should fall, due to dirt accumulation for example, the amplitude of the blade increases slightly (as described by SHO properties) so that the product of frequency and displacement (i.e., velocity) remains a constant. The other components of the circuit depend on the phase of the transducer signal for proper operation as discussed previously. The phase of the inputs to these components will have to be modified because of the new phase of the "velocity" transducer. In particular, 90° phase shift (lagging the velocity), will have to be introduced at the input of branch two of component one so that it will be in phase with the displacement. Similarly, phase shifter 41 at the input of component two can now be eleminated.

Various modifications and variations will no doubt occur to those skilled in the art to which this invention pertains. For example, amplitude reference amplifier 30 could be configured so that the reference voltage is applied through a resistor to the negative input of the amplifier while the positive input is grounded. This would accomplish the same electrical function provided the output of amplifier 30 is inverted. These and all other such variations which basically rely on the teachings through which this disclosure has advanced the art are properly considered within the scope of this invention.

I claim:

1. A mass-flow meter, includes:
   a mechanical vibratory element;
   an electromechanical actuator and sensing device for actuating a vibration of said element and for sensing the amplitude of vibration of said element;
   a feedback circuit means including input and output stages with an output coupled to said electromechanical actuating device and an input connected to said electromechanical sensing device, said feedback circuit means including a first, a second, and a third parallel circuit branches;
   said input stage coupled to said electromechanical device having a circuit to detect, amplify and adjust the phase of the sensor output so that it is in phase with the amplitude of the vibrator and with an output connected to each of said three parallel branches of said feedback circuit means;
   said first branch of said feedback circuit means for generating an ac voltage of frequency and amplitude to maintain the vibratory element at resonance with a constant amplitude, despite changes in the damping and resonant frequency of the vibrating element when applied to said electromechanical actuator through said output stage and including an amplifier to control the output amplitude of said first branch and having an output proportional to the mass flow of the fluid incident upon the vibratory element and thereby serving as a sensor of that quantity;
   said second branch of said feedback circuit means for generating a signal of a desired amplitude in phase with the velocity of said vibratory element and applied simultaneously to said electromechanical actuator through said output stage for the purpose of adjusting the mass-flow sensitivity of said mass-flow meter;
   said third branch of said feedback circuit means for generating an ac voltage in phase with the acceleration of said vibratory element and controlling the amplitude of this voltage so that when it is simultaneously applied to said electromechanical actuator through said output stage it maintains said vibratory element at its resonant frequency despite variations in those parameters which would normally change this frequency; and
   said output stage coupled to said electromechanical actuator including a summing amplifier which accepts inputs from each of said three branches of said feedback circuit means.

2. A meter as recited in claim 1 wherein said first branch includes control circuitry having a negative feedback amplifier coupled to a first reference voltage representing a desired vibrational amplitude, and to a second voltage representing the actual vibrational amplitude, and comparing said first and second voltage inputs and generating a first output signal proportional to the difference between said first and second voltage inputs which is a measure of the fluid mass flow, and applying said first output signal to one input of a multiplier circuit whose other input is an ac voltage at the resonance frequency of the oscillator so that the latter may be multiplied by a voltage adequate to keep the vibrator amplitude a constant when it is applied to said electromechanical actuator.

3. A meter as recited in claim 2, further comprising a full wave bridge to demodulate the output of said input stage to obtain a dc level proportional to the amplitude of the vibrator.

4. A meter as recited in claim 2, further comprising a phase lock loop circuit to generate an ac voltage at the resonance frequency of the oscillator using the signal from the input stage.

5. A meter as recited in claim 1, wherein said second branch includes a phase-shift circuit and a following amplifier to generate an ac voltage in phase with the velocity of the vibrator.

6. A meter as recited in claim 1, wherein said third branch includes a negative feedback amplifier which has a reference voltage applied to it representing the desired resonance frequency, and another dc voltage applied to it representing the actual resonance frequency, and comparing those inputs, and generating a third output proportional to the difference between the inputs, and applying said third output to one input of a multiplier circuit whose other input is an ac voltage at the resonance frequency and having a phase identical with the acceleration of the vibrator, so that when the latter is multiplied by the former and applied to the electromechanical actuator device, it will keep the resonance frequency at a desired value.

7. A meter as recited in claim 6, further comprising a dc voltage means for obtaining a dc voltage representing the resonance frequency of said vibratory element by applying the output of said input stage to a frequency to voltage converter.

8. A meter as recited in claim 6, further comprising an ac voltage means for obtaining an ac voltage at the resonance frequency and in phase with the vibrator acceleration by a phase-shift circuit using the output of the input stage.

9. A mass-flow meter having a mechanical vibratory element and including:
   an electromechanical actuator and sensing device for actuating a vibration of said element and for sensing the velocity of vibration of said element;
   a feedback circuit means including input and output stages with an output coupled to said electromechanical actuating device and an input connected to said electromechanical sensing device, said feedback circuit means including a first and a second parallel circuit branches;
   said input stage coupled to said electromechanical device having a circuit to detect, amplify and adjust the phase of the sensor output so that it is in phase with the velocity of the vibrator and with an output connected to each of said two parallel branches of said feedback circuit;

said first branch of said feedback circuit means generating an ac voltage of frequency and amplitude to maintain said vibratory element at resonance with a constant maximum velocity, despite changes in the damping and resonant frequency of said vibrating element, when applied to said electromechanical actuator through said output stage and including an amplifier to control the output amplitude of said first branch and having an output proportional to the mass-flow of fluid incident upon said vibratory element, and thereby serving as a sensor of that quantity, but independent of changes in the resonant frequency of said vibratory element;

said second branch of said circuit generating a signal of a desired amplitude in phase with the velocity of the vibrator and applied simultaneously to said electromechanical actuator through the output stage for the purpose of adjusting the mass-flow sensitivity of the meter; and said output stage applied to said electromechanical actuator including a summing amplifier which accepts inputs from each of said two branches of said feedback circuit means.

10. A meter as described in claim 9 in which said first branch of said feedback control circuitry includes a negative feedback amplifier which has a reference voltage applied to it which represents the desired maximum vibrational velocity and another applied voltage which represents the actual vibrational velocity, and comparing those inputs and generating an output proportional to the difference in the inputs which is a measure of the fluid mass flow, but independent of the resonance frequency of the vibrator, and applying this output to one input of a multiplier circuit whose other input is an ac voltage at the resonance frequency of the oscillator so that the latter may be multiplied by a voltage adequate to keep the vibrator velocity at a constant value when it is applied to the actuator.

11. A mass-flow meter having a mechanical vibratory element and including:

an electromechanical actuator and sensing device for actuating a vibration of the element and for sensing the amplitude of vibration of the element;

a feedback circuit means including input and output stages with an output coupled to said electromechanical actuating device and an input connected to said electromechanical sensing device, said feedback circuit means including a first, a second, and a third parallel circuit branches;

said input stage coupled to said electromechanical device having a circuit to detect, amplify and adjust the phase of the sensor output so that it is in phase with the amplitude of the vibrator and with an output connected to each of said two parallel branches of said feedback circuit;

said first branch of said feedback circuit means generating an ac voltage of frequency and amplitude to maintain the vibratory element at resonance with a constant amplitude, despite changes in the damping and resonant frequency of the vibrating element when applied to said electromechanical actuator through said output stage and including amplifier to control the output amplitude of said first branch and having an output proportional to the mass-flow of the fluid incident upon the vibratory element and thereby serving as a sensor of that quantity;

said second branch of said feedback circuit means for generating a signal of a desired amplitude in phase with the velocity of said vibratory element and applied simultaneously to said electromechanical actuator through said output stage for the purpose of adjusting the mass-flow sensitivity of said mass-flow meter;

said third branch of said feedback circuit means for generating an ac voltage in phase with the acceleration of said vibratory element and controlling the amplitude of this voltage so that when it is simultaneously applied to said electromechanical actuator through said output stage it maintains said vibratory element at its resonant frequency despite variations in those parameters which would normally change this frequency;

said output stage applied to said electromechanical actuator including a summing amplifier which accepts inputs from each of said three branches of said feedback circuit means;

said first branch including control circuitry having a negative feedback amplifier coupled to a first reference voltage representing a desired vibrational amplitude, and to a second voltage representing the actual vibrational amplitude, and comparing said first and second voltage inputs and generating a first output proportional to the difference between said first and second voltage inputs which is a measure of the fluid mass flow, and applying said first output to one input of a multiplier circuit whose other input is an ac voltage at the resonance frequency of the oscillator so that the latter may be multiplied by a voltage adequate to keep the vibrator amplitude a constant when it is applied to said electromechanical actuator;

a full wave bridge to demodulate the output of the input stage to obtain a dc level proportional to the amplitude of the vibrator;

a phase locked loop circuit to generate an ac voltage at the resonance frequency of the oscillator using the signal from the input stage;

a said second branch including a phase shift circuit and a following amplifier to generate an ac voltage in phase with the velocity of the vibrator;

said third branch including a negative feedback amplifier which has a reference voltage applied to it which represents the desired resonance frequency, and another dc voltage applied to it representing the actual resonance frequency, and comparing those inputs, and generating a third output proportional to the difference between the inputs, and applying said third output to one input of a multiplier circuit whose other input is an ac voltage at the resonance frequency and having a phase identical with the acceleration of the vibrator, so that when the latter is multiplied by the former and applied to the actuator it will keep the resonance frequency at a desired value;

dc voltage means for obtaining a dc voltage representing the resonance frequency of said vibratory element by applying the output of the input stage to a frequency to voltage converter; and an ac voltage means for obtaining an ac voltage at the resonance frequency and in phase with the vibrator acceleration by a phase shift circuit using the output of the input stage.

12. A mass-flow meter having a mechanical vibratory element and including:

an electromechanical actuator and sensing device for actuating a vibration of the element and for sensing the amplitude of vibration of the element;

a feedback circuit means including input and output stages with an output coupled to said electromechanical actuating device and an input connected to said electromechanical sensing device, said feedback circuit means including a first and a second parallel circuit branches;

said input stage coupled to said electromechanical device having a circuit to detect, amplify and adjust the phase of the sensor output so that it is in phase with the velocity of the vibrator and with an output connected to each of said two parallel branches of said feedback circuit;

said first branch of said circuit means generating an ac voltage of frequency and amplitude to maintain said vibratory element at resonance with a constant maximum velocity, despite changes in the damping and resonant frequency of said vibrating element, when applied to said electromechanial actuator through the output stage and an amplifier within said first branch which controls the output amplitude of said first branch and having an output proportional to the mass flow of fluid incident upon said vibratory element, and thereby serving as a sensor of the quantity, but independent of changes in the resonant frequency of said vibratory element;

said second branch of said circuit generating a signal of a desired amplitude in phase with the velocity of the vibrator and applied simultaneously to said electromechanical actuator through the output stage for the purpose of adjusting the mass-flow sensitivity of the meter;

said output stage applied to said electromechanical actuator including a summing amplifier which accepts inputs from each of said two branches of said feedback circuit means; and said first branch having a negative feedback amplifier which has a reference voltage applied to it which represents the desired maximum vibrational velocity, and another voltage representing the actual vibrational velocity, and comparing those inputs and generating an output proportional to the difference in the inputs which is a measure of the fluid mass flow but independent of the resonance frequency of the vibrator, and applying this output to one input of a multiplier circuit whose other input is an ac voltage at the resonance frequency of the oscillator so that the latter may be multiplied by a voltage adequate to keep the vibrator velocity at a constant value where it is applied to the actuator.

* * * * *